(12) United States Patent
Fehn

(10) Patent No.: US 7,393,966 B2
(45) Date of Patent: Jul. 1, 2008

(54) PROCESS FOR PREPARING PLATINUM CATALYST

(75) Inventor: Armin Fehn, Mehring (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/923,754

(22) Filed: Oct. 25, 2007

(65) Prior Publication Data

US 2008/0103322 A1    May 1, 2008

(30) Foreign Application Priority Data

Oct. 27, 2006  (DE) ..................... 10 2006 050 863

(51) Int. Cl.
*C07F 15/00*    (2006.01)

(52) U.S. Cl. ..................................... 556/136

(58) Field of Classification Search ................. 556/136
See application file for complete search history.

(56) References Cited

OTHER PUBLICATIONS

J. Chem. Soc. (1968), pp. 1993-2001.
J. of the Am. Chem. Soc. 92 (1970) pp. 1274-1278.
Johnson, B.F.G. et al., "Metal beta-diketone complexes. Part V. The interaction of beta-diketones with diene complexes of palladium (II) and platinum (II)", Journal of the Chemical Society, A, 1968, p. 1993-2001.

*Primary Examiner*—P. Nazario-Gonzalez
(74) *Attorney, Agent, or Firm*—Brooks Kushman P.C.

(57) ABSTRACT

Platinum 1,3-diketo compounds are prepared by stirring a dichloroplatinum compound and a diketo compound in a keto solvent at below 10° C. for from 5 minutes to 90 minutes and isolating the reaction product. The product is obtained in high purity suitable for use as a catalyst for preparing polymer articles suitable for use in the medical and food industries.

14 Claims, No Drawings

PROCESS FOR PREPARING PLATINUM CATALYST

BACKGROUND OF THE INVENTION

1. Field of the Invention

The subject invention pertains to an improved process for preparing platinum 1,3-diketo compounds in high purity.

2. Background Art

For the production of moldings which are used in the medical sector or come into contact with foods, e.g. baking trays, storage containers, it is necessary to meet demanding purity requirements which are specific in terms of particular impurities.

The catalyst which is used in crosslinking of the moldings which are used in the medical sector or come into contact with foods therefore also has to meet specific purity requirements; in particular, the platinum catalyst has to have a high purity and must not contain any toxicologically unacceptable impurities or by-products and nevertheless has to be able to be produced economically.

It is known from J. Chem. Soc. (1968) 1993-2001 that cylooctadiene-$PtCl_2$ reacts with two molar equivalents of thalium acetylacetonate in chloroform at room temperature to form acacCODPtacac. After stirring, the thalium chloride precipitate is filtered off, the filtrate is evaporated to dryness and the product is obtained by recrystallization from petroleum ether. No information is given about the yield or about the purity of the product.

This literature method is not suitable for a production process since, firstly, the toxic solvent chloroform (risk phrases: 22-38-40, 48/20/22) is used and, secondly, as an even more serious objection, the very toxic compound thalium acetylacetonate (R: 26/28-33-51/53) is used. It is not possible to rule out that residual thalium compounds remain in the product.

J. Am. Chem. Soc. 92 (1970) 1274-1278 discloses the preparation of 3-(1-acetyl-2-oxopropyl)bicyclo[2.2.1]hept-5-en-2-yl)-(2,4-pentan-edionato-O,O')platinum from dichloro(endo-bicyclopentadiene)platinum(II), sodium carbonate in a molar excess and acetylacetone in excess. For this purpose, the abovementioned mixture is stirred at room temperature for 4 days. The sodium chloride and sodium carbonate are subsequently filtered off and the filtrate is evaporated to dryness. The resulting product is purified by column chromatography using dichloromethane as eluent and is subsequently recrystallized from dichloromethane. The yield is 55%.

The method has serious disadvantages for a preparation on a production scale, e.g. long reaction times of 4 days and the low yield. In addition, the product has to be purified by column chromatography.

SUMMARY OF THE INVENTION

It is therefore an object of the invention to improve the prior art, in particular to make available a platinum catalyst which is suitable for crosslinking of moldings which are used in the medical sector or come into contact with foods. The invention provides a process for preparing platinum 1,3-diketo compounds, which comprises stirring a dichloroplatinum compound and a diketo compound in a keto solvent at below 10° C. for from 5 minutes to 1 hour and isolating the reaction product, preferably by filtration and removal of the solvent.

DETAILED DESCRIPTION OF THE PREFERRED EMBODIMENTS

The dichloroplatinum compound preferably has an aliphatic or cyclic diolefin radical. The radical is more preferably norbornadiene or cyclooctadiene.

The diketo compound is preferably a compound of the formula:

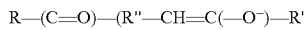

where

R can be methyl, ethyl, phenyl, allyl, R—O

R' can be methyl, ethyl, phenyl, allyl

R" can be hydrogen, methyl, ethyl, phenyl.

The diketones are preferably the sodium or potassium salts of acetylacetonate, 2,4-(3-methyl)pentanedionate, 2,4-(3-ethyl)pentanedionate, 2,4-(3-phenyl)pentanedionate, 2,4-hexanedionate, 3,5-heptanedionate, 1,1,1-trifluoro-2,4-pentanedionate, or hexafluoro-2,4-pentanedionate. Furthermore, salts of acetocarboxylic esters, preferably the sodium salt of methyl acetoacetate, can also be used in place of diketonates.

In addition, a mixture of diketone (acetylacetone, 2,4-(3-methyl)pentanedione, 2,4-(3-ethyl)pentanedione, 2,4-(3-phenyl)pentanedione, 2,4-hexanedione, 3,5-heptanedione, 1,1,1-trifluoro-2,4-pentanedione, hexafluoro-2,4-pentanedione) in combination with, preferably, sodium carbonate or acetocarboxylic esters, preferably ethyl acetoacetate, methyl acetoacetate, preferably in combination with sodium carbonate can also be used in place of the diketonate.

The diketo compound is preferably the potassium or sodium salt of 2,4-(3-methyl)pentanedionate, 2,4-(3-phenyl)pentanedionate, 3,5-heptanedionate, potassium acetylacetonate, or sodium acetylacetonate, more preferably potassium acetylacetonate or sodium acetylacetonate.

The purity of the diketo compound is also important and preferably should preferably be greater than 90% by weight, more preferably greater than 95% by weight, and most preferably greater than 97% by weight. The diketo compound is preferably used in an amount of from 1.7 to 2.1 mol per mol of platinum compound, more preferably from 1.9 to 2.0 mol per mol of platinum compound.

The keto solvent is preferably acetone, methyl ethyl ketone, methyl propyl ketone, methyl butyl ketone, cyclohexanone, diethyl ketone, dibutyl ketone, acetone, or acetophenone, more preferably acetone, or methyl ethyl ketone. The keto solvent is preferably used in an amount of from 5 to 30 ml per gram of platinum compound, more preferably from 10 to 20 ml per gram of platinum compound.

The reaction is preferably carried out at temperatures which are below room temperature, with a reaction at below 0° C. being advantageous. The reaction temperature is preferably from 10° to −200° C., more preferably from 0° to −90° C., yet more preferably from −10° to −80° C., and most preferably from −10° to −50° C.

The reaction times are preferably in the range of from 5 minutes to 90 minutes, more preferably from 5 minutes to 1 hour, and most preferably from 20 minutes to 45 minutes.

In the process of the invention, the respective compounds are stirred and the reaction mixture is preferably filtered at the end of the reaction. The product is subsequently dried, preferably under reduced pressure. If the keto solvent cannot be removed completely even after drying for a number of hours, even at elevated temperature, the product is preferably suspended in alkanes such as pentane, heptane and the like and after stirring for about 2 hours is filtered off and the precipitate is once again dried under reduced pressure.

Preference is given to preparing diketo complexes of dichloro(norbornadiene)platinum(II) by the process of the invention.

The process of the invention has the advantage that it enables platinum 1,3-diketo compounds having a purity of up to 97.5% to be prepared and is thus particularly suitable for the production of moldings which are used in the medical sector or come into contact with foods, e.g. packaging containers, storage containers, baking trays, etc.

EXAMPLES

Comparative Example 1

In the laboratory, 1.00 g (2.79 mmol) of dichloro(norbornadiene)platinum(II) (MW=358.1) and 0.80 g (5.79 mmol) of potassium acetylacetonate (MW=138.2) were suspended in 15 ml of acetone, stirred at room temperature (RT) for 2 hours and subsequently filtered. The product was subsequently dried under reduced pressure. Since the acetone could not be completely removed even after drying for a number of hours, even at elevated temperature, the product was suspended in 20 ml of heptane, stirred for 2 hours and filtered and the precipitate was once again dried under reduced pressure. This gave 0.83 g of a brown powder, which corresponds to a yield of 61%.

The $^1$H-NMR spectrum using an internal standard (trimethyl benzenetricarboxylate) indicated a purity of the target compound of about 78%. By-products were clearly visible in the spectrum but could not be identified.

Comparative Example 2

Comparative Example 1 was repeated using dichloromethane as solvent instead of acetone. The powder obtained was somewhat lighter in color but not of higher purity.

Comparative Examples 3-5

Purification experiments were carried out on the product from experiment 1 or 2. The products were firstly washed with various solvents, and since this treatment was unsuccessful, recrystallization experiments from a) dichloromethane/pentane, b) THF/diethyl ether and c) acetone/diethyl ether were carried out. This was still unable to improve the purity.

Comparative Example 6

Comparative Example 1 was repeated using 0.9 g (6.5 mmol) of sodium acetylacetonate monohydrate. The target product obtained had a purity of 80.5%.

Comparative Example 7

Laboratory experiment 6 was repeated using 1.0 g (7.3 mmol) of sodium acetylacetonate monohydrate. The product purity was only about 60%.

Comparative Example 8

Comparative Example 6 was repeated with the exception that the mixture was stirred overnight at RT. The purity of the product was only about 30%.

Comparative Example 9

Comparative Example 1 was repeated, this time however using 0.80 g of potassium acetylacetonate hemihydrate from Fluka having a purity of 97%. The purity of the product obtained was 89.5%.

Comparative Example 10

Comparative Example 9 was repeated but dichloro(norbornadiene)platinum and acetone were initially placed in the reaction vessel and cooled to −78° C. 0.83 g of potassium acetylacetonate hemihydrate from Fluka was subsequently added, the mixture was thawed to RT and stirred at RT for 3 hours. Work-up of the mixture in a manner analogous to experiment 1 gave a cream-colored powder having a purity of 90.9%.

Comparative Example 11

Example 10 was repeated, this time however using 0.87 g of potassium acetylacetonate hemihydrate from Fluka. The purity of the product obtained was 84.7%.

Example 12

Example 10 was repeated with the mixture being stirred at −78° C. for 30 minutes instead of at RT for 3 hours. The purity of the product obtained was 97.6%.

Example 13

Example 12 was repeated with the reaction temperature being maintained at −20° C., the reaction time being 45 minutes and the solvent being taken off at 0° C. The purity of the product obtained was 97.9%.

Example 14

Example 10 was repeated with the reaction temperature being maintained at −10° C. after the addition of potassium acetylacetonate, the reaction time being 45 minutes and the solvent subsequently being taken off at about −10° C. The purity of the product obtained was 97.4%.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing platinum 1,3-diketo compounds, which comprises stirring a dichloroplatinum compound and a diketo compound in a keto solvent at below 10° C. for from 5 minutes to 90 minutes and isolating the reaction product.

2. The process of claim 1, wherein the dichloroplatinum compound contains an aliphatic or cyclic diolefin radical.

3. The process if claim 2, wherein the diolefin radical is norbornadiene or cyclooctadiene.

4. The process of claim 1, wherein at least one diketo compound is selected from the group consisting of 2,4-(3-methyl)pentanedionate, 2,4-(3-phenyl)pentanedionate, 3,5-heptanedionate, potassium acetylacetonate, sodium acetylacetonate.

5. The process of claim 2, wherein at least one diketo compound is selected from the group consisting of 2,4-(3- methyl)pentanedionate, 2,4-(3-phenyl)pentanedionate, 3,5-heptanedionate, potassium acetylacetonate, sodium acetylacetonate.

6. The process of claim 3, wherein at least one diketo compound is selected from the group consisting of 2,4-(3-methyl)pentanedionate, 2,4-(3-phenyl)pentanedionate, 3,5-heptanedionate, potassium acetylacetonate, sodium acetylacetonate.

7. The process of claim 2, wherein the keto solvent is selected from the group consisting of acetone, methyl ethyl ketone, methyl propyl ketone, methyl butyl ketone, cyclohexanone, diethyl ketone, dibutyl ketone, acetone, acetophenone, and mixtures thereof.

8. The process of claim 3, wherein the keto solvent is selected from the group consisting of acetone, methyl ethyl ketone, methyl propyl ketone, methyl butyl ketone, cyclohexanone, diethyl ketone, dibutyl ketone, acetone, acetophenone, and mixtures thereof.

9. The process of claim 4, wherein the keto solvent is selected from the group consisting of acetone, methyl ethyl ketone, methyl propyl ketone, methyl butyl ketone, cyclohexanone, diethyl ketone, dibutyl ketone, acetone, acetophenone, and mixtures thereof.

10. The process of claim 5, wherein the keto solvent is selected from the group consisting of acetone, methyl ethyl ketone, methyl propyl ketone, methyl butyl ketone, cyclohexanone, diethyl ketone, dibutyl ketone, acetone, acetophenone, and mixtures thereof.

11. The process of claim 6, wherein the keto solvent is selected from the group consisting of acetone, methyl ethyl ketone, methyl propyl ketone, methyl butyl ketone, cyclohexanone, diethyl ketone, dibutyl ketone, acetone, acetophenone, and mixtures thereof.

12. The process of claim 1, wherein the purity of the platinum 1,3-diketo compound is greater than 95%.

13. The process of claim 1, wherein the purity of the platinum 1,3-diketo compound is greater than 97%.

14. The process of claim 1, wherein the purity of the platinum 1,3-diketo compound is greater than 97.4%.

* * * * *